United States Patent
Boulos et al.

(10) Patent No.: US 6,914,073 B2
(45) Date of Patent: Jul. 5, 2005

(54) VITAMIN FORMULATION FOR CARDIOVASCULAR HEALTH

(75) Inventors: Atef Boulos, Rockaway, NJ (US); Jatin Desai, Fairport, NY (US); Neil Martin, Succasunna, NJ (US); Robert Stillman, Union, NJ (US); Marion Udwin, Closter, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/047,583

(22) Filed: Jan. 14, 2002

(65) Prior Publication Data

US 2002/0172721 A1 Nov. 21, 2002

Related U.S. Application Data

(63) Continuation-in-part of application No. 09/512,512, filed on Feb. 24, 2000, now abandoned, which is a continuation-in-part of application No. 09/271,810, filed on Mar. 18, 1999, now abandoned.

(51) Int. Cl.$^7$ .................. A61K 31/355; A61K 9/14; A61K 9/20; A61K 47/00
(52) U.S. Cl. .................. 514/458; 424/464; 424/465; 424/489; 424/490; 514/770; 514/781; 514/904; 514/905; 514/960; 514/961
(58) Field of Search .................. 424/465, 469, 424/489, 490, 600, 464; 514/458, 769, 770, 781, 904, 905, 960, 961, 964, 965

(56) References Cited

U.S. PATENT DOCUMENTS

| | | | |
|---|---|---|---|
| 2,858,215 A | 10/1958 | Espoy et al. | 426/73 |
| 3,608,083 A | 9/1971 | Bunnell et al. | 514/458 |
| 4,486,435 A | * 12/1984 | Schmidt et al. | 514/251 |
| 4,603,143 A | 7/1986 | Schmidt | 514/458 |
| 4,717,561 A | 1/1988 | Krivak et al. | 423/335 |
| 5,571,441 A | 11/1996 | Andon et al. | 252/1 |
| 5,925,381 A | * 7/1999 | Boyle et al. | 424/499 |
| 5,948,443 A | 9/1999 | Riley et al. | 424/643 |
| 5,997,915 A | 12/1999 | Bailey et al. | 426/72 |
| 6,030,645 A | * 2/2000 | Tritsch et al. | 424/490 |

FOREIGN PATENT DOCUMENTS

| | | |
|---|---|---|
| EP | 0 595 005 | * 5/1994 |
| EP | 0 867 177 A1 | 2/1998 |
| WO | 92/05780 | 4/1992 |

* cited by examiner

*Primary Examiner*—S. Mark Clardy
*Assistant Examiner*—Frank Choi
(74) *Attorney, Agent, or Firm*—Terence J. Bogie; Laurelee A. Duncan

(57) ABSTRACT

The invention concerns a composition containing a high level of Vitamin E in encapsulated form, preferably as beadlets or spray dried, and a high level of silicates. The composition is compressible into tablets or caplets that do not leach out Vitamin E into the tablet matrix during compression and/or storage. The composition preferably contains vitamins and minerals in doses optimized for cardiovascular health.

12 Claims, No Drawings

VITAMIN FORMULATION FOR CARDIOVASCULAR HEALTH

RELATED U.S. APPLICATION DATA

This application is a continuation-in-part of co-pending application U.S. Ser. No. 09/512,512 filed Feb. 24, 2000, now abandoned, which was a continuation-in-part of co-pending application U.S. Ser. No. 09/271,810 filed Mar. 18, 1999, now abandoned.

FIELD OF THE INVENTION

This invention concerns a nutritional supplement composition, more particularly, a multivitamin/multimineral formulation, which is designed to benefit cardiovascular health.

The composition of the invention contains a high concentration of Vitamin E that is encapsulated, preferably in the form of beadlets or spray dried, and, surprisingly, is compressable into tablets and caplets that do not leach out the Vitamin E oil during compression or long-term storage.

BACKGROUND OF THE INVENTION

Cardiovascular disease is the leading cause of death in the United States and many other countries. Nutritional factors are widely recognized as playing a role in preventing, delaying the onset of and/or slowing the progression of arteriosclerosis and coronary heart disease. Attempts have been made in the prior art to design multivitamin supplements specifically for heart health. For example, U.S. Pat. No. 5,770,215 discloses, a multivitamin composition containing various vitamins, minerals, and acetylsalicylic acid. Another example is WO 98/41195, which discloses a nutritional supplement containing at least one flavonoid and folic acid or folate.

Heretofore, a multivitamin/multimineral optimized for cardiovascular health containing increased levels of Vitamin E and Folic Acid, low levels of iron, as well as containing mixed carotenoids, has been unknown.

SUMMARY OF THE INVENTION

The present invention concerns a multivitamin/multimineral composition designed for cardiovascular health. As used herein the multivitamin/multimineral composition of the invention will sometimes be referred to as the "vitamin formulation" or the "vitamin composition." The vitamin formulation comprises:

about 400 to about 1000 μg Folic Acid, about 100 to about 1200 International Units (IU) Vitamin E, about 0 to about 8 mg iron, and about 200 to 6000 μg mixed carotenoids.

The vitamin composition of the invention preferably contains Folic Acid in an amount of about 450 to about 1000 μg, more preferably about 500 to about 900 μg, and most preferably about 600 to about 800 μg.

The vitamin composition of the invention contains Vitamin E in an amount of at least 100 IU, preferably about 200 to about 1000 IU, more preferably about 300 to about 900 IU, and most preferably about 400 to about 800 IU.

The vitamin composition of the invention preferably contains Iron in an amount of about 0 to about 7 mg, more preferably about 0 to about 6 mg, and most preferably about 0 to about 4 mg.

The vitamin composition of the invention preferably contains mixed carotenoids in an amount of about 250 to about 3000 μg, more preferably about 300 to about 2000 μg, and most preferably about 350 to about 1000 μg.

In addition to containing Vitamin E, Folic Acid, optionally iron, and mixed carotenoids, the composition of the invention also optionally and preferably contains one or more of Vitamin $B_6$, Vitamin $B_{12}$, and Magnesium.

The vitamin composition of the invention preferably contains Vitamin $B_6$ in an amount of about 2 to about 200 mg, more preferably about 4 to about 150 mg, even more preferably about 6 to about 100 mg, and most preferably about 10 to about 50 mg.

The vitamin composition of the invention preferably contains Vitamin $B_{12}$ in an amount of about 2 to about 800 μg, more preferably about 10 to about 600 μg, even more preferably about 15 to about 400 μg, and most preferably about 25 to about 200 μg.

The vitamin composition of the invention preferably contains Magnesium in an amount of about 50 to about 450 mg, more preferably about 75 to about 400 mg, even more preferably about 100 to about 350 mg, and most preferably about 125 to about 300 mg.

In addition to containing Vitamin E, Folic Acid, optionally iron, and mixed carotenoids, as well as optionally containing one or more of Vitamin $B_6$, Vitamin $B_{12}$, and magnesium, the composition of the invention also optionally and preferably contains one or more of Vitamin C, Selenium, Vitamin K and β-carotene.

The vitamin composition of the invention preferably contains Vitamin C in an amount of about 80 to about 1000 mg, more preferably about 90 to about 900 mg, even more preferably about 100 to about 700 mg, and most preferably about 120 to about 600 mg.

The vitamin composition of the invention preferably contains Selenium in an amount of about 20 to about 500 μg, more preferably about 30 to about 400 μg, even more preferably about 40 to about 300 μg, and most preferably about 50 to about 200 μg.

The vitamin composition of the invention preferably contains β-carotene in an amount of about 75 to about 5000 μg, more preferably about 100 to about 3000 μg, even more preferably about 150 to about 2000 μg, and most preferably about 200 to about 1500 μg.

The vitamin composition of the invention preferably contains Vitamin K in an amount of about 0 to about 200 μg, more preferably about 6 to about 150 μg, even more preferably about 8 to about 100 μg, and most preferably about 10 to about 75 μg.

DETAILED DESCRIPTION OF THE INVENTION

All of the amounts and ranges of ingredients of the vitamin formulation of the invention given herein are on a per dose basis. A single dose of the vitamin formulation is typically suitable for the daily requirements of most patients, although in some situations multiple doses per day are indicated. Most preferably, the dose is contained in one or two dosage units.

Folic Acid is a B complex vitamin. It is water-soluble and occurs naturally in green plants, fresh fruit, and yeast. Folic acid along with Vitamins $B_{12}$ (cyanocobalamin) and $B_6$ play a key part in homocysteine metabolism. Several medical studies have suggested that moderately elevated serum levels of homocysteine in the general population are perhaps associated with atherosclerosis and coronary heart disease (CHD), although data to the contrary exists. It has been suggested that a 5 μmole/L increment in homocysteine level confers a relative increase in risk of coronary heart disease of 1.6 for men, and 1.8 for women (see C. J. Boushey, et al., JAMA, 274, 1049–1057, 1995). Also, it has been demonstrated that inadequate folic acid or folate intake is the main determinant of the homocysteine—related increase in carotid artery thickening, another significant manifestation of atherosclerotic disease. The mechanism by which elevated blood homocysteine causes accelerated atherosclerosis has not been clearly established (see, for example, E. B. Rimm, et al., JAMA, 279(5), 359–364, Feb. 4, 1998; K. S. McCully, JAMA, 279(5), 392–393, Feb. 4, 1998; J. Selhub, JAMA, 270(22), 2693–2698, Dec. 8, 1993; and C. J. Boushey, et al., JAMA, 274 (13), 1049–1057, Oct. 4, 1995). It is not at present clear whether hyperhomocysteinemia is an independent risk factor for CHD, or is merely a marker of low folate status, which may independently affect the risk of CHD (see J. Selhub et al., JAMA, 270, 2693–2698, 1993). Several ongoing randomized trials are addressing whether supplements will decrease the incidence of CHD.

As used herein the term "Folic Acid" is intended to include all chemical derivatives of folic acid that function equivalently to folic acid, such as mono and polyglutamyl folates, dihydro and tetrahydro folates, methyl and formyl folates.

As used herein the term "Vitamin $B_6$" is intended to include all chemical derivatives of Vitamin $B_6$ that function equivalently to Vitamin $B_6$. Vitamin $B_6$ can be selected from hydrochloride salts or 5-phosphates of pyridoxine, pyridoxamine, or pyridoxal. The preferred Vitamin $B_6$ is pyridoxine hydrochloride.

As used herein the term "Vitamin $B_{12}$" is intended to include all chemical derivatives of Vitamin $B_{12}$ that function equivalently to Vitamin $B_{12}$. Sources of Vitamin $B_{12}$ are, for example, cyanocobalamin, methylcobalamin, adenosylcobalamin, hydroxocobalamin and the like. Cyanocobalamin is highly preferred.

Antioxidant vitamins such as Vitamin E and Vitamin C may play a role in interfering with metabolic mechanisms that lead to cardiovascular disease (see, for example, A. A. Quyymi, Am. J. Med. 105 (1A): 325–395, Jul. 6, 1998; G. D Plotnick et al., JAMA, 278(20): 1682–1686, Nov. 26, 1997; M. Mietus-Snyder, et al., J. of Pediatrics: 133 (1), 35–40, July 1998; and D. M. Gilligan et al., JACC, 24(7): 1611–1617, December, 1994). The vitamin composition of the present invention contains increased levels of Vitamin E relative to conventional multivitamin/multimineral formulations, and preferably contains increased levels of Vitamin C. The increased level of Vitamin C is to support plasma antioxidant activity, and, in particular, to help regenerate Vitamin E from the tocopheroxyl radical or otherwise preserve Vitamin E levels (see I. Jialal et al., J. Clin. Invest., 87: 597–601, 1991).

Epidemiologic data suggest that the beneficial effects of generous antioxidant intake via supplementation may be of more than modest magnitude, particularly when relatively high doses are consumed. The largest epidemiologic study to date (see M. J. Stampfer et al., N Engl J Med: 328, 1444–9, 1993) reported results from the Nurses Health Study (NHS), a prospective cohort study. After 679,485 person-years of follow-up in this 8-year study, women in the highest fifth of the cohort for Vitamin E consumption had a relative risk (RR) of major coronary disease of 0.66. Most of the effect was attributable to Vitamin E from supplements, as all the women in the top 20% of Vitamin E intake were users of either multivitamins or specific Vitamin E supplements. Significant associations were observed only for intake of 100 IU/day or more; lower does of Vitamin E supplements had little effect. Women who used Vitamin E supplements for less than 2 years had little apparent benefit, but use for 2 years or longer was associated with a 41% reduction in risk of coronary heart disease (see E. B. Rimm et al., JAMA, 278: 359–64, 1998).

More data supporting the protective effects of Vitamin E supplement use are emerging. In a large prospective 4-year assessment of 39,910 men in the Health Professionals Follow-up Study (HPFS), Rimm et al., (see N Engl J Med., 328: 1450–6, 1993) reported that, compared with men in the lowest fifth of Vitamin E intake, men in the highest fifth had an age-adjusted relative risk of coronary disease of 0.59. Similar to that seen in the NHS, a significant reduction in risk of coronary disease was limited to those with intake of Vitamin E supplements, with the maximal reduction in coronary risk noted among men consuming 100 to 250 IU/day. Losonczy et al (see Am. J Clin. Nutr. 1996; 64: 190–196) followed 11,178 subjects aged 67 to 105 years of age in the Established Populations for Epidemiologic Studies of the Elderly (EPESE) study. After an average of 8.5 years of follow-up, the participants who reported the use of Vitamin E supplements at baseline had a relative risk of 0.59 for death from coronary disease as compared with those not taking supplements.

Two randomized, controlled clinical trials with Vitamin E have been completed. In the Alpha-Tocopherol Beta-Carotene Lung Cancer Prevention (ATBC) study, (see N Engl J Med., 330: 1029–1035, 1994), men assigned to Vitamin E (50 mg/day) had only a very small, nonsignificant reduction in risk for mortality from ischemic heart disease. The results are entirely consistent with those observed in the NHS and the HPFS (see American Heart Association News Releases. 1996. American Heart Association's president lists top 10 heart and stroke research advances for 1996). In the observational studies, intake of low-dose Vitamin E, in the range used in the ATBC trial (50 mg/day), also was not associated with any material decrease in the risk of coronary disease. In the HPFS, (see E. B. Rimm et al., N Engl J Med., 328: 1450–6, 1993) men consuming vitamin E supplements in doses of 25 to 99 IU/d had a nonsignificant relative risk of 0.78. As further indication that higher doses of Vitamin E may be necessary, in a double-blind, placebo-controlled secondary prevention trial Stephens et al (see N Engl J Med., 330, 1029–1035, 1994) found that men taking 400 or 800 IU/day of vitamin E had a strong (77%) reduction in nonfatal myocardial infarction. After an average follow-up of 1.5 years, the 1035 patients with angiographically proven atherosclerosis assigned to Vitamin E had a relative risk of major cardiovascular events of 0.53. This effect was similar in magnitude to that reported in the observational studies.

The term "Vitamin E" is intended to include all functionally equivalent forms of tocopherol; however, d-alpha-tocopherol, dl-alpha-tocopherol, and/or their esters including acetates and succinates (particularly the acetate form) generally can be used as a source for Vitamin E. Other sources of Vitamin E include beta-tocopherol, gamma-tocopherol, the tocotrienols and their esters, tocopheryl nicotinate, polymeric tocopherol and the like.

The term "Vitamin C" is intended to include all forms of Vitamin C such as L-ascorbic acid, D-ascorbic acid, DL-ascorbic acid, D-araboascorbic acid, dehydroascorbic acid, esters of ascorbic acid or their salts, and the like.

Survey data indicate that along with the recent phenomenon of reduced prevalence of iron deficiency in the United States, a concomitant rise in serum ferritin concentrations in men and postmenopausal women has also been documented. These findings have led to concern about the effectiveness of the physiological mechanisms for limiting storage accumulation in normal individuals and carriers of the hemochromatosis gene when dietary iron content is high. Furthermore, recent epidemiological observations suggest that a modest increase in body iron stores is a possible risk factor for ischemic heart disease and cancer; however, a causal relationship has yet to be proven (see S. R. Lynch et al., J. Nutr. 126: 2400S–2409S, 1996). At least seven epidemiologic studies have found a positive association between CHD and various indicators of body iron. Conversely, 18 epidemiologic studies have found a negative or no association.

The present invention contains lower levels of iron than present in many multivitamin formulations. Iron, if present in the vitamin composition, can be in forms used in multivitamins, multiminerals and nutritional supplements, for example, ferrous fumarate, ferrous gluconate, ferrous sulfate, ferric acetate, carbonyl iron, and the like can be used.

Over the past several years, the epidemiologic evidence to support the cardioprotective effect of carotenoids has grown, though the evidence supporting a specific benefit of β-carotene is inconsistent and one large clinical trial suggests an adverse effect (see E. B. Rimm, Cur. Opin. Cardiol., 12: 188–194, 1997). Over 600 carotenoid compounds have been identified, of which at least 40 have been isolated in foods. The most common, in descending order, are lycopene, β-carotene, β-cryptoxanthin, lutein, α-carotene, and zeaxanthin (see N. I. Krinsky, Ann. Rev. Nutr., 13: 561–587, 1993). It is possible that other carotenoids that are correlated with β-carotene in the diet and the blood might be important factors. β-carotene is typically present in other vitamin formulations at levels up to about 5000 $\mu$g. A unique feature of the vitamin formulation of the invention is that the level of β-carotene (commonly comprising 20% of Vitamin A activity) has been decreased, and the vitamin formulation contains mixed carotenoids. By the term "mixed carotenoids" is meant a combination of at least two of the following carotenoids: α-carotene, β-carotene, lycopene, lutein, zeaxanthin, and cryptoxanthin. Preferably the composition of the invention contains three or more, four or more, five or more, and most preferably all six of the above-noted carotenoids. The vitamin formulation of the invention preferably contains a positive amount of β-carotene. The vitamin formulation of the invention contains less than 5000 $\mu$g β-carotene, preferably less than 4000 $\mu$g, more preferably less than 2000 $\mu$g and most preferably less than 1000 $\mu$g. Preferred amounts of each specific carotenoid are listed below:

|  | Preferred | More preferred |
| --- | --- | --- |
| α-carotene | about 10 to about 800 $\mu$g | about 50 to about 500 $\mu$g |
| β-carotene | about 25 to about 2000 $\mu$g | about 125 to about 1250 $\mu$g |
| Lycopene | about 5 to about 800 $\mu$g | about 25 to about 250 $\mu$g |
| Lutein | about 10 to about 700 $\mu$g | about 45 to about 450 $\mu$g |
| Zeaxanthin | about 0.4 to about 200 $\mu$g | about 2 to about 100 $\mu$g |
| Cryptoxanthin | about 0.05 to about 20 $\mu$g | about 0.1 to about 10 $\mu$g |

Data exist that support the hypothesis that diets rich in potassium, magnesium, and cereal fiber reduce the risk of stroke, particularly among hypertensive men (see A. Asherio et al., Circulation, 98: 1198–1204, 1998). Additionally, the Artherosclerosis Risk in Communities (ARIC) Study in four U.S. communities has found magnesium intake to be inversely associated with carotid artery thickness in women; this cross-sectional study additionally suggests that low serum magnesium levels and inadequate dietary magnesium intake may be related to the etiologies of cardiovascular disease, hypertension, diabetes, and artherosclerosis (see J. Ma et al., J. Clin. Epidemiol., 48: 927–940, 1995).

The Magnesium in the vitamin formulation of the invention can be in any form used in multivitamins, multiminerals, and nutritional supplements. A preferred form of magnesium is magnesium oxide.

The Selenium in the vitamin formulation of the invention can be in any form used in multivitamins, multiminerals, and nutritional supplements. A preferred form of Selenium is sodium selenate.

Vitamin K can be selected from Vitamin $K_1$ (phytonadione, phylloquinone) or Vitamin $K_2$ (menaquinone) and their salts and derivatives. Vitamin $K_1$, is highly preferred.

The vitamin composition of the invention preferably contains at least one of the following additional organic nutrients: Vitamin A, Vitamin D, Thiamin, Riboflavin, Niacin or Niacinamide, Biotin, and Pantothenic Acid. It is preferred that the vitamin composition of the invention contains two or more, three or more, four or more, five or more, and most preferably all of the above-noted additional organic nutrients listed in this paragraph.

Also, the vitamin formulation of the invention preferably contains at least one of the following additional minerals: Calcium, Chromium, Copper, Manganese, Molybdenum, and Zinc. It is preferred that the vitamin composition of the invention contains two or more, three or more, four or more, five or more, and most preferably all the above-noted additional minerals listed in this paragraph.

Additionally, the vitamin composition may optionally contain one or more of the following additional minerals: Boron, Chloride, Iodine, Nickel, Phosphorous, Potassium, Silicon, Tin, Vanadium, and the like.

In general, regarding the additional organic nutrients and additional minerals, it is preferred that the vitamin composition of the invention contains at least about 3% of United States Reference Daily Intakes ("RDI"), if defined, as delineated in the Code of Federal Regulations (21 C.F.R. Chapter 1, Apr. 1, 1997), of each of the particular additional organic nutrients and/or additional minerals that are present; preferably between about 50% and about 1400% of the R.D.I.; more preferably between about 100% and 500% of the R.D.I. More particular preferred amounts of each additional organic nutrient and each additional mineral are given on the next page:

|  | Preferred | More Preferred |
| --- | --- | --- |
| Vitamin A | About 200 IU to about 10000 IU | about 2500 IU to about 5000 IU |
| Vitamin D | About 200 IU to about 800 IU | about 400 IU to about 600 IU |
| Thiamin ($B_1$) | About 0.06 mg to about 12 mg | about 1.5 mg to about 7.5 mg |
| Riboflavin ($B_2$) | About 0.068 mg to about 13.6 mg | about 1.7 mg to about 8.5 mg |
| Pantothenic acid | About 0.4 mg to about 800 mg | about 10 mg to about 500 mg |
| Niacin | About 0.8 mg to about 160 mg | about 20 mg to about 100 mg |
| Biotin | About 12 mcg to about 800 mcg | about 20 mcg to about 300 mcg |
| Calcium | About 40 mg to about 2000 mg | about 50 mg to about 1200 mg |
| Chromium | About 4.8 mcg to about 960 mcg | about 25 mcg to about 600 mcg |
| Copper | About 0.08 mg to about 9 mg | about 1 mg to about 6 mg |
| Iodine | About 6 mcg to about 1200 mcg | about 150 mcg to about 750 mcg |
| Manganese | About 0.08 mg to about 10 mg | about 2 mg to about 8 mg |
| Molybdenum | About 3 mcg to about 350 mcg | about 75 mcg to about 250 mcg |
| Zinc | About 0.6 mg to about 60 mg | about 15 mg to about 30 mg |
| Boron | About 0 mcg to about 1200 mcg | about 0 mcg to about 750 mcg |
| Chloride | About 0 mg to about 12000 mg | about 0 mg to about 8000 mg |
| Nickel | About 0 mcg to about 40 mcg | about 0 mcg to about 25 mcg |
| Phosphorus | About 0 mg to about 4000 mg | about 0 mg to about 2400 mg |
| Potassium | About 0 mg to about 6000 mg | about 0 mg to about 4000 mg |
| Silicon | About 0 mg to about 50 mg | about 0 mg to about 10 mg |
| Tin | About 0 mcg to about 80 mcg | about 0 mcg to about 50 mcg |
| Vanadium | About 0 mcg to about 80 mcg | about 0 mcg to about 50 mcg |

Vitamin D can be selected from, for example, cholecalciferol (D3), ergocalciferol (D2), and their biologically active metabolites and precursors such as, 1-alpha-hydroxy Vitamin D, 25-hydroxy Vitamin D, 1,25-dihydroxy Vitamin D and the like. Vitamin D as cholecalciferol is highly preferred. The hydrochloride and nitrate salts of thiamin and thiamin alkyl disulfides such as the prophyldisulfide, tetrahydrofurfuryl disulfide, o-benzoyl disulfide can be used in the present invention. The hydrochloride and nitrate salts are highly preferred. The sources of riboflavin are selected, for example, from crystalline riboflavin coenzyme forms of riboflavin such as flavin adenine dinucleotide, flavin adenine mononucleotide, riboflavin 5-phosphate and their salts. Riboflavin is highly preferred. Niacin may comprise, for example, nicotinic acid, nicotinamide (niacinamide), the coenzyme forms of niacin such as nicotinamide adenine dinucleotide, and nicotinamide adenine dinucleotide phosphate. Particularly preferred are nicotinamide and nicotinic acid. Biotin for use in the vitamin composition can be selected from oxybiotin, biocytin, biotinol and the like. Biotin is highly preferred. For pantothenic acid the sources can be in the form of salts such as calcium pantothenate or as panthenol. Calcium pantothenate is the highly preferred source of pantothenic acid.

The minerals in the vitamin formulation of the invention are typically in salt form. Such salts can be any of the well known salts including carbonate, oxide, hydroxide, chloride, sulfate, phosphate, gluconate, lactate, acetate, fumarate, citrate, malate, amino acids, and the like for the cationic minerals and sodium, potassium, calcium, magnesium, and the like for the anionic minerals. However the particular salt used and the level will depend upon their interaction with other supplement ingredients.

Other additives may be incorporated in the vitamin mineral composition of the present invention. Such additives include; pyridoxine; inositol; para-aminobenzoic acid; flavonoids; aspirin; cholesterol-lowering pharmaceutical agents such as those commonly referred to as "statins", for example pravastatin, lovastatin, simvastatin, atorvastin, and the like; amino acids such as glutamic acid, L-glutamine, L-arginine, glycine, L-glutathione, L-lysine, tyrosine, proline, L-cysteine, choline, and the like; phosopholipids; tocotrienols; selected herbals such as green tea, garlic, ginseng, hawthorne, alfalfa, gingko, grape seed extract, and the like; coenzyme Q10; alpha lipoic acid, omega-3 and omega-6 fatty acids; fish oils such as eicosapentenoic acid, docosahexaenoic acid, and the like; β-sitosterol; β-sitostanol; red yeast rice, pectin, betaine HCl; and the like.

In another embodiment of the invention, a dietary fiber supplement such as oat bran or other natural fiber source may also be added to the composition.

Typically the vitamin formulation will further include pharmaceutically acceptable components such as lactose, glucose, sucrose, corn starch, potato starch, cellulose esters such as cellulose acetate, ethyl cellulose, magnesium stearate, calcium silicate, precipitated silica, talc, fatty acids such as stearic acid, microcrystalline cellulose, carnauba wax and the like. Diluents and other additives such as one or more pharmaceutically acceptable binding agents, fillers, supports, thickening agents, taste-improving agents, coloring agents, preservatives, stabilizers, regulators, emulsifiers, flow agents, absorbents, and the like or mixtures thereof may be used depending on the form of the composition employed.

In addition to providing the aforementioned composition, the invention also includes a method for administering the vitamin composition of the invention to an individual who has or is at risk of having artherosclerosis or coronary heart disease in dosages effective to aid in preventing, delaying the onset of and/or slowing the progression of atherosclerosis or coronary heart disease. Typical effective doses are 1–6, 1–5, 1–4, 1–3, 1–2 and most preferably 1 dose per day. More particularly, the invention includes a method for orally administering the aforesaid composition to an individual who has, is at risk of, or may be at risk of atherosclerosis, coronary heart disease, myocardial infarction, transient ischemic attacks, strokes, blood clots, and other cardiac care conditions. The vitamin composition of the present invention is particularly useful in people having one or more major and/or minor risk factors for cardiovascular disease. Major risk factors include low levels of HDL cholesterol, high serum cholesterol and various cholesterol fractions, hypertension, diabetes mellitus, advancing age ($\geq 45$ years for men; $\geq 55$ years or premature menopause without estrogen replacement therapy for women), and cigarette smoking.

Minor risk factors include obesity, physical inactivity, family history of premature CHD, hypertriglyceridemia, small low-density lipoprotein particles, increased lipoprotein (a), increased serum homocysteine, and abnormalities in several coagulation factors (e.g., platelet hyper reactivity, high levels of hemostatic proteins [e.g., fibrinogen and factor IV], defective fibrinolysis, and hyperviscosity of the blood), metabolic syndrome and/or insulin resistance. The vitamin composition is preferably administered orally but administration may be parenteral, sublingual, intranasal, transdermal, or buccal. Suitable forms for the vitamin composition include tablets, capsules, caplets, lozenges (including fast melt forms), syrups, granules, solutions, nasal sprays, aerosols, suppositories, transdermal patches, and suspensions which contain unit dose(s) of the composition for administration once, several times a day, or weekly. The vitamin composition of the invention will typically be administered orally as a tablet, caplet, or a capsule. A single dose of the vitamin formulation in tablet, caplet, or capsule form can be one, two, three, four, five, six or more tablets, caplets or capsules. It is preferred to have a single dose in two tablets, caplets, or capsules. Dosage forms of the invention such as tablets, caplets, gel tabs, capsules, liquid and sustained release formulations, and the like can be formulated and prepared according to manufacturing techniques well known in the pharmaceutical industry.

Another aspect of the present invention is that the required levels of ingredients, particularly Vitamin E, can be formulated into a low number of dosage units, e.g., one or two. This low number of dosage units to achieve a single effective dose is an advantage over the prior art. Therefore, the present invention also includes a process for preparing a dosage unit having high levels of Vitamin E. The process of the invention is not limited to preparing the vitamin formulation of the invention, but is applicable to any vitamin, mineral, and/or nutritional supplement having high levels of Vitamin E. Thus, the present invention is also directed to a process for preparing a tablet or caplet having at least 100 IU Vitamin E, and other vitamins and minerals, comprising contacting Vitamin E in encapsulated form, preferably beadlets or spray dried, most preferably as beadlets, and other vitamins and minerals with silica and silicate, in amounts and under conditions effective to form a tablet or caplet, wherein the tablet or caplet formed does not visibly leach out Vitamin E oil from the encapsulated Vitamin E during compression or when stored at about room temperature for 12–24 months. In the present invention the encapsulated Vitamin E, most preferably in the form of beadlets containing up to 75% Vitamin E oil, is mixed with precipitated silica and preferably calcium silicate. In this step the silica and the silicate ingredients form protective layers surrounding the Vitamin E beadlets. These protective layers absorb any Vitamin E oil that might be squeezed out of the beadlets during compression. The tablet or caplet of the process of the invention contains at least 100 IU Vitamin E, typically at least 200 IU Vitamin E. The encapsulated Vitamin E in the process of the invention is preferably contacted or blended with microcrystalline cellulose and/or anhydrous magnesium silicate (talc), in addition to silica and silicate. The tablet or caplet prepared by the process of the invention preferably contains other excipients commonly used in the pharmaceutical art. The other vitamins and minerals used in the process of the invention can be any or all of the vitamins and minerals discussed herein for use in the vitamin composition of the invention. A preferred process of the invention comprises preparing a vitamin premix containing encapsulated Vitamin E and other vitamins, preparing a mineral premix, blending microcrystalline cellulose, silica, silicate, talc, the vitamin premix, and the mineral premix to form a homogeneous blend, and compressing the blend under conditions sufficient to form a tablet or caplet.

Surprisingly, in this invention, the combination of precipitated silica, calcium silicate and talc results in a blend which is compressible using standard or commonly available tablet presses and is free or substantially free of problems such as an unfavorable change in dissolution rate or processing problems such as sticking, picking, low hardness, capping, and the like that occur when compression forces of tabletting rupture the beadlets and release Vitamin E oil into the tablet matrix.

In the process of the invention it is preferred that the contacting or blending is carried out in a mixer from about 5 minutes to about 5 hours at a temperature of about 5° C. to about 50° C. and said compressing is carried out at a pressure of about 3 kilo newtons to about 100 kilo newtons. It is also preferred that the proportions of Vitamin E:precipitated silica:calcium silicate be 2–50:1–10:1–10.

Additionally, the process of the invention comprises using conventional processing techniques. The product can be made by either direct compression, or slugging some of the ingredients, milling the slugs, blending with remaining ingredients then compressing as appropriate. The product can also be made into tablets using the wet granulation technique, drying the wet mass, blending with other ingredients, then compressing into tablets.

The incorporation of a high concentration of Vitamin E in a composition adapted for compression into tablets or caplets presents many difficulties. Primarily, during compression and/or over time the Vitamin E oil leaches out of the Vitamin E beadlets, or spray dried Vitamin E, into the tablet matrix, resulting in loss of tablet integrity and/or undesirable change in the tablet's dissolution rate.

The present inventors have surprisingly found that a certain combination of excipients in conjunction with Vitamin E (preferably Vitamin E acetate) in spray dried form, or in the form of beadlets, enables the production of compressed tablets or caplets that are stable. Encapsulated Vitamin E oil in the form of beadlets, or in spray dried form, is referred to herein as "encapsulated Vitamin E." In this context "stable" means that no Vitamin E leaches out of the encapsulated Vitamin E into the tablet matrix when the tablet is stored at room temperature for a period of at least twelve months from the date of manufacture of the tablet or when stored for three months at 40° C. and a relative humidity of 75%. Preferably, tablets and caplets prepared by compressing the composition of the instant invention show no leaching of Vitamin E from the encapsulated Vitamin E into the tablet or caplet matrix when the tablet or caplet is stored at room temperature for two years or when stored for six months at 40° C. and 75% relative humidity.

The surprising stability of the high Vitamin E containing tablets and caplets prepared from the compositions of the present invention is attributable to the calcium silicate and precipitated silica content of such compositions.

In order to produce stable tablets or caplets containing a high concentration of Vitamin E, it is essential that the composition that is to be compressed into the tablets or caplets contain a level of calcium silicate and silica greatly exceeding levels of such agents heretofore employed by those skilled in the art of tablet and caplet production.

According to "The Theory and Practice of Industrial Pharmacy" by Lachman, Lieberman, and Kanig, Third Edition, copyright 1986, p 328:

"Materials used as glidants, or flow promoters, are typically talc at a 5% concentration, corn starch at a 5 to 10% concentration, or colloidal silicas such as Cab-O-Sil, Syloid, or Aerosil in 0.25 to 3% concentrations."

In contradistinction thereto, the percentage of total silicate in the composition of the present invention is over 4%, preferably at least about 5%, more preferably from about 5% to about 8%. Such levels of silicate would not be employed by one skilled in the art as high levels of silicate are known to disadvantageously reduce the flow of compositions intended to be compressed into tablets or caplets. While the high levels of silicate contained in the compositions of the present invention do indeed act to reduce composition flow when the composition is tabletted, they surprisingly prevent the high Vitamin E content of the tablet from leaching out of the encapsulated Vitamin E into the tablet matrix and causing a loss of tablet or caplet integrity and/or an undesireable change in the tablet's or caplet's dissolution rate.

The calcium silicate component of the compressible composition of the invention is present in the range of about 1 to about 10%, preferably, it is present in an amount of about 4.5%.

The precipitated silica is present in an amount of from about 0.5 to about 10%, preferably, it is present in an amount of about 4%.

The total of the amounts of calcium silicate and precipitated silica present in the composition should be over 4%, preferably at least about 5%, more preferably from about 5% to about 8%.

Additionally, the ratio of the amount of encapsulated Vitamin E to the total amount of precipitated silica and calcium silicate contained in the composition should be from 3:1 to 6:1.

Stability of the tablets or caplets produced from the composition of the invention is further enhanced by including in the composition from about 5 to about 50% microcrystalline cellulose and about 1 to about 5% talc. Preferably about 30% microcrystalline cellulose is employed.

The microcrystalline cellulose increases tablet hardness circumventing the need for high compression force that would squeeze Vitamin E oil out of the encapsulated Vitamin E into the tablet matrix. The combination of the calcium silicate, precipitated silica and microcrystalline cellulose employed in the tablet and caplet formulation of the invention greatly increases cohesive and binding interaction between the different particles without adversely affecting the dissolution profile of the produced tablet or caplet.

Talc functions to improve flow characteristics of the formulation and to decrease sticking of the tablets/caplets to the faces of the tablet punches.

Other agents useful in tablet and caplet production may be employed, for example, crospovidone and stearic acid.

Although not wishing to be bound by any particular theory, it may well be that the combination of calcium silicate and precipitated silica helps absorb any Vitamin E squeezed out of the encapsulated Vitamin E during tablet compression and binds it so that it does not leach into the tablet matrix and destroy tablet integrity and/or appearance. Syloid® 244FP and Syloid® 72FP are particularly preferred precipitated silicas.

Emcocel® 90M is a particularly preferred microcrystalline cellulose.

Micro-Cel® C is a particularly preferred calcium silicate.

The encapsulated Vitamin E is preferably Vitamin E acetate and is preferably in the form of beadlets or is spray dried; most preferably it is in the form of beadlets.

Vitamin E tablets or caplets prepared in accordance with the present invention can contain as much as 600 IU of Vitamin E per tablet or caplet. Size of the Tablet or caplet is the limiting factor. If, however, one or more other vitamins and/or minerals are to be incorporated along with the Vitamin E in the tablet or caplet, the overall size of the tablet or caplet might be so large as to make swallowing of same difficult. This problem can be circumvented by dividing the concentration of each ingredient in half and increasing the dose to two tablets or caplets. Since each tablet or caplet would be smaller in size, a dose of two tablets or caplets would be easier to swallow.

Cab-O-Sil® has been used in tablet production in the prior art but at much lower levels. The total silicates content (the total of silica and calcium silicate) of the compressible Vitamin E compositions of the present invention is much greater than levels previously employed in the art. As noted earlier, the levels employed in the composition of the instant invention actually reduce flow (i.e., glidancy) and as such would not be used by one skilled in the art. The present inventors have surprisingly discovered that these high levels are necessary to successfully prepare compressed tablets or caplets that contain a high concentration of Vitamin E (at least 100 IU preferably at least 200 IU, per tablet or caplet) and that are "stable" (as previously defined herein).

An increase in compression force without a corresponding increase in tablet or caplet hardness indicates that Vitamin E oil has leached out of the encapsulated Vitamin E into the tablet or caplet matrix. Similarly, an increase in disintegration time, without a corresponding increase in hardness, as compression force is increased, indicates that Vitamin E oil has leached out of the encapsulated Vitamin E into the tablet or caplet matrix and may even have coated the tablet or caplet thereby impeding disintegration.

Surprisingly the high level of Vitamin E, contained in the tablets and/or caplets prepared from the composition of the present invention, is retained within the tablet or caplet matrix.

This is substantiated by the fact that when the composition of the invention is subjected to increasing compressive force both disintegration time and hardness increase.

Having described the invention in detail, it will be apparent that numerous modifications and variations are possible.

The following examples are offered only to illustrate the invention, and should not be interpreted as a limitation thereon.

EXAMPLE 1

Preparation of Compositions of the Invention

Formulation I

Mineral Premix

| ITEM | INGREDIENT | mg/dose |
|---|---|---|
| 1 | Cupric Sulfate, Purified anhyd. | 4.273 |
| 2 | Zinc Oxide, Light | 19.050 |
| 3 | Manganese Sulfate, monohydrate | 6.280 |
| 4 | Sodium Selenate | 0.193 |
| 5 | Sodium Molybdate Dihydrate | 0.209 |
| 6 | Chromium Chloride, Hexahydrate | 0.274 |
| 7 | Potassium Iodide | 0.220 |
| 8 | Ferrous Fumarate | 12.736 |

-continued

Mineral Premix

| ITEM | INGREDIENT | mg/dose |
|---|---|---|
| 9 | Calcium Carbonate DC | 115.000 |
| 10 | Microcrystalline Cellulose | 54.291 |
| | Sub Total (Min. Premix) | 212.526 |

Vitamin Premix

| ITEM | INGREDIENT | mg/dose |
|---|---|---|
| 1 | Thiamine Mononitrate, USP FCC | 3.752 |
| 2 | Pyridoxine HCl, USP | 28.521 |
| 3 | Cyanocobalamin (Vitamin B12) 1% | 4.050 |
| 4 | Folic Acid, USP | 0.811 |
| 5 | Riboflavin, USP, F.C.C. | 4.403 |
| 6 | Niacinamide, USP granular | 22.267 |
| 7 | Silicon Dioxide Colloidal | 0.738 |
| 8 | Biotin, 1% Trituration | 3.300 |
| 9 | Vitamin A Acetate, Dry, 500 A | 13.500 |
| 10 | Mixed Carotenoid | 15.000 |
| 11 | Vitamin D3, Dry | 6.000 |
| 12 | Vitamin K1, Phytonadione 1% SD | 1.925 |
| 13 | Calcium Pantothenate | 15.333 |
| | Sub Total (Vitamin Premix) | 119.600 |

Final Blend

| Item | Ingredient | mg/dose |
|---|---|---|
| 1 | Mineral Premix | 212.526 |
| 2 | Vitamin Premix | 119.600 |
| 3 | Ascorbic Acid 90%, granular | 162.712 |
| 4 | Vitamin B Acetate 75% S.D. | 640.000 |
| 5 | Precipitated Silica | 91.000 |
| 6 | Calcium Silicate | 104.000 |
| 7 | Magnesium Oxide granular | 287.817 |
| 8 | Microcrystalline Cellulose | 696.345 |
| 9 | Crospovidone | 130.000 |
| 10 | Stearic Acid, USP | 78.000 |
| 11 | Talc, USP | 78.000 |
| | Total | 2600.000 |

Color Coating Suspension

| Item | Ingredient | mg/dose |
|---|---|---|
| 1 | Pharmaceutical color mix | 52.000 |
| 2 | Distilled Water* | 360.000 |
| | Total | 412.000 |

*Evaporates off during processing

Formulation II

Vitamin Premix

| Item | Ingredient | mg/dose |
|---|---|---|
| 1 | Thiamine Mononitrate, USP, FCC | 3.752 |
| 2 | Pyridoxine HCl, USP | 28.521 |
| 3 | Cyanocobalamin (Vitamin B12) | 4.050 |
| 4 | Folic Acid, USP | 0.811 |
| 5 | Riboflavin, USP, FCC | 4.403 |
| 6 | Niacinamide, USP | 22.267 |
| 7 | Silicon Dioxide Colloidal | 0.738 |
| 8 | Biotin, 1% Trituration | 3.300 |
| 9 | Vitamin A Acetate, Dry, 500A | 13.500 |
| 10 | Mixed Carotenoid | 15.000 |
| 11 | Vitamin D3, dry | 6.000 |
| 12 | Vitamin K1, Phytonadione 1% SD | 1.925 |
| 13 | Calcium Pantothenate | 15.333 |
| | Sub total (Vitamin Premix) | 119.600 |

Final Blend

| Item | Ingredient | mg/dose |
|---|---|---|
| 1 | Vitamin Premix | 119.600 |
| 2 | Ascorbic Acid granular | 162.712 |
| 3 | Vitamin E Acetate beadlets | 640.000 |
| 4 | Precipitated Silica | 73.000 |
| 5 | Calcium Silicate | 84.000 |
| 6 | Microcrystalline Cellulose | 562.688 |
| 7 | Crospovidone | 104.000 |
| 8 | Stearic Acid, USP | 57.000 |
| 9 | Talc, USP | 57.000 |
| | Total | 1860.000 |

Color Coating Suspension

| Item | Ingredient | mg/dose |
|---|---|---|
| 1 | Pharmaceutical color mix | 52.000 |
| 2 | Distilled Water* | 360.000 |
| | Total | 412.000 |

*Evaporates off during processing

Formulation III

| Item | Ingredient | mg/dose |
|---|---|---|
| 1 | Folic Acid, USP | 0.811 |
| 2 | Cyanocobalamin (Vitamin $B_{12}$) | 4.050 |
| 3 | Pyridoxine HCl, USP | 28.521 |
| 4 | Mixed Carotenoid | 15.000 |
| 5 | Ascorbic Acid granular | 162.712 |
| 6 | Vitamin B Acetate beadlets | 640.000 |
| 7 | Precipitated Silica | 70.000 |
| 8 | Calcium Silicate | 80.000 |
| 9 | Microcrystalline Cellulose | 560.906 |
| 10 | Crospovidone | 98.000 |
| 11 | Stearic Acid, USP | 55.000 |
| 12 | Talc, USP | 55.000 |
| | Total | 1770.000 |

| Color Coating Suspension | | |
|---|---|---|
| Item | Ingredient | mg/dose |
| 1 | Pharmaceutical color mix | 44.000 |
| 2 | Distilled Water* | 305.000 |
| | Total | 349.000 |

*Evaporates off during processing

Formulation IV

| Item | Ingredient | mg/dose |
|---|---|---|
| 1 | Mixed Carotenoid | 15.000 |
| 2 | Ascorbic Acid granular | 162.712 |
| 3 | Vitamin E Acetate beadlets | 640.000 |
| 4 | Precipitated Silica | 70.000 |
| 5 | Calcium Silicate | 80.000 |
| 6 | Microcrystalline Cellulose | 560.288 |
| 7 | Crospovidone | 95.000 |
| 8 | Stearic Acid, USP | 51.000 |
| 9 | Talc, USP | 51.000 |
| | Total | 1725.000 |

| Color Coating Suspension | | |
|---|---|---|
| Item | Ingredient | mg/dose |
| 1 | Pharmaceutical color mix | 44.000 |
| 2 | Distilled Water* | 305.000 |
| | Total | 349.000 |

*Evaporates off during processing

PROCESSING INSTRUCTIONS

Mineral Premix

1. Into a tumble mixer or any appropriate mixer add the following through a Comil equipped with 0.032" screen:
   a. Cupric Sulfate
   b. Zinc Oxide
   c. Manganese Sulfate
   d. Trace Mineral Trituration
   e. Ferrous Fumarate
   f. Microcrystalline Cellulose
   g. Calcium Carbonate DC
2. Blend for a sufficient amount of time.
3. Discharge into PE-lined Drums and hold for use in the final blend.

Vitamin Premix

1. Add to a v-Blender or any appropriate mixer through a 10 mesh screen the following materials: Thiamine Mononitrate, Riboflavin, Pyridoxine HCl, Vit. B12, Niacinamide, Folic Acid, Biotin, Calcium Pantothenate and collodial silicon dioxide.
2. Through 5 mesh screen add the following ingredients into the V-Blender: Vitamin A Acetate, mixed Carotenoid, Vitamin D3 and Vitamin K1 1%.
3. Blend for a sufficient amount of time.

Vitamin E Premix

1. Into a PK—Double Cone blender, or a low shear blender, charge Vitamin E beadlets, precipitated silica and calcium silicate and, optionally, magnesium silicate hydrous (talc) or combinations thereof.
2. Blend for a sufficient amount of time.
3. Discharge into PE-lined drums and hold for use in the final mix.

Final Blend

1. Into a PK Double Cone mixer or an appropriate mixer, charge the following ingredients:
   a. Vitamin Premix
   b. Vitamin E Premix
   c. Ascorbic Acid granular
   d. Mineral Pre-mix
   e. Crospovidone
   f. Microcrystalline Cellulose
2. Blend for a sufficient amount of time.
3. Add to the final blend through 20 mesh screen Stearic Acid and Talc and blend for another 5 minutes.
4. Discharge into PE-lined drums and hold for tabletting.
5. Compress into tablets using suitable tooling.

Color Coat

1. In a clean, tared stainless steel tank with cover equipped for agitation, prepare the color film coating mixture.
2. Using a conventional coating equipment, spray onto tablets enough suspension to achieve a good uniform color coat.

The following Example 2 is illustrative of the preparation of stable tablets containing a high dose of Vitamin E in each tablet in accordance with the present invention. It should be appreciated that although the Example contains only Vitamin E other Vitamins and/or minerals could also be incorporated in the formulation. Most desirably, vitamins and minerals as disclosed earlier in this application as being designed specifically for optional cardioprotective effect.

EXAMPLE 2

| Preparation of Vitamin E Stand Alone Product-600 IU E/tablet | | |
|---|---|---|
| Item | Ingredient | mg/dose |
| 1 | Vitamin E Acetate beadlets | 960.000 |
| 2 | Precipitated Silica | 86.300 |
| 3 | Calcium Silicate | 98.600 |
| 4 | Microcrystalline Cellulose | 850.000 |
| 5 | Crospovidone | 123.300 |
| 6 | Stearic Acid | 74.000 |
| 7 | Talc | 74.000 |
| | Total | 2266.200 |

We claim:

1. A composition comprising:
   (i) an amount of encapsulated Vitamin E such that when the composition is divided into unit doses each unit dose contains at least 100 International Units Vitamin E,
   (ii) from about 0.5% to about 10% by weight based on total weight of the composition, of precipitated silica,
   (iii) from about 1% to about 10% by weight, based on total weight of the composition, of calcium silicate,
   (iv) from about 5% to about 50% by weight, based on total weight of the composition, of microcrystalline cellulose,
   (v) from 0 to about 5% by weight, based on total weight of the composition, of talc; and
   (vi) an amount of vitamins in addition to Vitamin E and an amount of additional minerals;

wherein the precipitated silica and the calcium silicate is present in a total amount of over 4% by weight, based on total weight of the composition; the encapsulated Vitamin E and the total amount of silica and calcium silicate is present in a ratio of from 3:1 to 6:1; and the composition is compressible into stable tablet or caplet unit doses containing the encapsulated Vitamin E in the matrix of said tablet or caplet in which no Vitamin E leaches out of encapsulated Vitamin E into the tablet or caplet matrix when the tablet or caplet is stored at room temperature for a period of at least twelve months from the date of manufacture of the tablet or caplet or when stored for three months at 40° C. and a relative humidity of 75%.

2. The composition, as claimed in claim 1, wherein each unit dose contains at least 200 International Units Vitamin E.

3. The composition, as claimed in claim 1, wherein the total amount of precipitated silica and calcium silicate is at least about 5%.

4. The composition, as claimed in claim 1, wherein the total amount of precipitated silica and calcium silicate is from about 5% to about 8%.

5. The composition, as claimed in claim 1, wherein the calcium silicate is present in an amount of about 4.5% and the precipitated silica is present in an amount of about 4%.

6. The composition, as claimed in claim 1, wherein the talc is present in an amount of from about 1% to about 5%.

7. The composition, as claimed in claim 1, wherein the proportion of encapsulated Vitamin E:precipitated silica:calcium silicate is 2–50:1–10:1–10.

8. The composition, as claimed in claim 1, wherein the microcrystalline cellulose is present in an amount of about 30%.

9. The composition, as claimed in claim 1, wherein the encapsulated Vitamin E is Vitamin E acetate beadlets.

10. The composition, as claimed in claim 1, wherein the encapsulated Vitamin E is spray dried Vitamin E.

11. The composition, as claimed in claim 1, wherein the additional minerals and vitamins are selected from Folic Acid, iron, lycopene, β-carotene, β-cryptoxanthin, lutein, α-carotene, zeaxanthin, Vitamin $B_6$ Vitamin $B_{12}$, Magnesium, Vitamin C, Selenium, Vitamin K, Vitamin A, Vitamin D, Thiamin, Riboflavin, Niacin, Biotin, Pantothenic Acid, Calcium, Chromium, Copper, Manganese, Molybdenum, Zinc, Boron, Chloride, Iodine, Nickel, Phosphorous, Potassium, Silicon, Tin, Vanadium, and mixtures thereof.

12. A method of providing a cardiovascular benefit to a human comprising orally administering to said human a daily dose of one or more stable tablets or caplets prepared by compressing the composition of claim 1, said Vitamin E, additional minerals and vitamins being present in amounts effective to decrease homocysteine level in said human, and wherein each unit does contains at least 100 International Units Vitamin E.

* * * * *